US010324055B2

(12) United States Patent
McCoy

(10) Patent No.: US 10,324,055 B2
(45) Date of Patent: Jun. 18, 2019

(54) PROCESS VARIABLE TRANSMITTER WITH TERMINAL BLOCK MOISTURE SENSOR

(71) Applicant: Rosemount Inc., Shakopee, MN (US)

(72) Inventor: Steven John McCoy, Eden Prairie, MN (US)

(73) Assignee: ROSEMOUNT INC., Shakopee, MN (US)

( * ) Notice: Subject to any disclaimer, the term of this patent is extended or adjusted under 35 U.S.C. 154(b) by 135 days.

(21) Appl. No.: 14/871,884

(22) Filed: Sep. 30, 2015

(65) Prior Publication Data
US 2017/0089856 A1    Mar. 30, 2017

(51) Int. Cl.
G01N 27/22    (2006.01)
G01D 11/24    (2006.01)
G01D 21/02    (2006.01)

(52) U.S. Cl.
CPC ........... *G01N 27/223* (2013.01); *G01D 11/24* (2013.01); *G01D 11/245* (2013.01); *G01D 21/02* (2013.01)

(58) Field of Classification Search
CPC .................................................. G01N 27/223
See application file for complete search history.

(56) References Cited

U.S. PATENT DOCUMENTS

| | | | | |
|---|---|---|---|---|
| 5,424,649 A * | 6/1995 | Gluck | ................... | G01N 27/223 137/78.5 |
| 5,481,200 A | 1/1996 | Voegele et al. | | |
| 6,701,274 B1 * | 3/2004 | Eryurek | ................. | G01D 3/022 702/130 |
| 8,334,788 B2 | 12/2012 | Hausler et al. | | |
| 9,237,684 B2 | 1/2016 | Ruf et al. | | |
| 2003/0107385 A1 * | 6/2003 | Shon | ..................... | G01N 27/121 324/694 |
| 2004/0008041 A1 * | 1/2004 | Davis | .................. | G01N 27/225 324/664 |
| 2005/0211466 A1 | 9/2005 | Kayser | | |
| 2007/0103170 A1 | 5/2007 | DeHart | | |
| 2011/0010120 A1 | 1/2011 | Wehrs et al. | | |

(Continued)

FOREIGN PATENT DOCUMENTS

| | | |
|---|---|---|
| DE | 10 2011 088 302 | 6/2013 |
| EP | 1 206 689 | 12/2004 |

(Continued)

OTHER PUBLICATIONS

International Search Report and Written opinion for PCT/US2016/052438, dated Mar. 6, 2017.
(Continued)

*Primary Examiner* — Clayton E. LaBalle
*Assistant Examiner* — Dennis Hancock
(74) *Attorney, Agent, or Firm* — Westman, Champlin & Koehler, P.A.

(57) ABSTRACT

A process variable transmitter for use in an industrial process includes a housing having a cavity formed therein. The housing has a barrier which divides the cavity into first and second cavities. Measurement circuitry in the first cavity is configured to measure a process variable of the industrial process. A terminal block assembly is located in the second cavity. A moisture sensor has an electrical characteristic which changes based upon the presence of moisture in the second cavity.

24 Claims, 8 Drawing Sheets

(56) References Cited

U.S. PATENT DOCUMENTS

2011/0215944 A1* 9/2011 Hausler .......... G01D 11/24
340/870.02
2014/0074303 A1 3/2014 Haynes et al.
2016/0139071 A1 5/2016 Nakano et al.
2016/0381822 A1 12/2016 Hausler et al.

FOREIGN PATENT DOCUMENTS

| JP | 56-112637 | 9/1981 |
|----|-----------|--------|
| JP | 58-186461 | 12/1983 |
| JP | 2003-508742 | 3/2003 |
| JP | 2005-265746 | 9/2005 |
| JP | 2013-521496 | 6/2013 |
| WO | WO 01/16571 | 3/2001 |
| WO | 2014/191619 A1 | 12/2014 |
| WO | WO 2014/203553 | 12/2014 |

OTHER PUBLICATIONS

Hygrosens: "Elektrolythischer Feuchtesensor EFS-10", Aug. 31, 2006, XP055346068, Retrieved from the Internet: URL: http://www.mikrocontroller.net/attachment/42166/EFS10.pdf on Feb. 15, 2017, 3 pages.
"Single-key QTouch Touch Sensor" ATMEL, pp. 1-25, 2013.
Invitation to Pay Additional Fees from PCT/US2016/052438, dated Dec. 5, 2016.
Communication from European Patent Application No. 16778533.6, dated May 14, 2018.
Office Action from Chinese Patent Application No. CN201610191201.3, dated Sep. 21, 2018.
Office Action from Chinese Patent Application No. 201610191201.3, dated Mar. 12, 2019.
Office Action from Japanese Patent Application No. 2018-516442, dated Feb. 27, 2019.

* cited by examiner

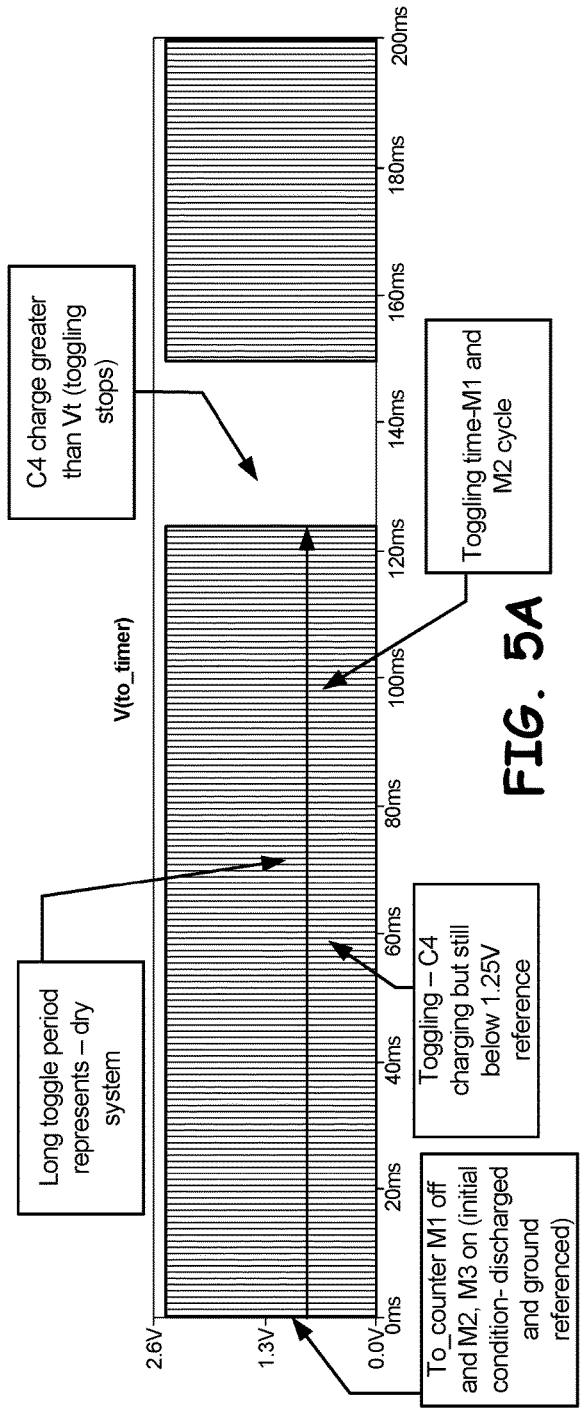

PROCESS VARIABLE TRANSMITTER WITH TERMINAL BLOCK MOISTURE SENSOR

BACKGROUND

The present invention relates to industrial process control or monitoring systems. In particular, the present invention relates to process variable transmitters configured to sense process variables in such systems.

Process variable transmitters are used in industrial process control environments to monitor process variables. Such transmitters couple to a process fluid and provide measurements related to the process. Process variable transmitters can be configured to monitor one or more process variables associated with fluids in a process plant, such as slurries, liquids, vapors and gases in chemical, pulp, petroleum, gas, pharmaceutical, food and other fluid processing plants. Example monitored process variables include pressure, temperature, flow, level, pH, conductivity, turbidity, density, concentration, chemical composition or other properties of fluids. Typically, the process variable transmitters are located at remote locations, usually in a field, and send information to a centralized location such as a control room. Process variable transmitters sense process variables in a variety of applications, including oil and gas refineries, chemical storage tank farms, or chemical processing plants. In many instances, this requires the process variable transmitters to be located in a harsh environment.

Some types of process variable transmitters include a housing divided into two separate compartments. One compartment contains electrical circuitry and the other compartment contains a terminal block used to couple to a process control loop. One such configuration is shown in U.S. Pat. No. 5,546,804. In such a configuration, the compartment which contains the terminal block may collect moisture due to condensation, leaks, or other sources. Such moisture may cause errors in data transmitted by the process variable transmitter and may even lead to ultimate failure of the device. One known technique to detect such moisture is by monitoring changes in electrical characteristics of the process control loop. Such techniques are shown and described in, for example, US Publication No. 2011/0010120, to Wehrs et al., entitled PROCESS VARIABLE TRANSMITTER WITH TWO-WIRE PROCESS CONTROL LOOP DIAGNOSTICS and assigned to Rosemount Inc.

SUMMARY

A process variable transmitter for use in an industrial process includes a housing having a cavity formed therein. The housing has a barrier which divides the cavity into first and second cavities. Measurement circuitry in the first cavity is configured to measure a process variable of the industrial process. A terminal block assembly is located in the second cavity. A moisture sensor has an electrical characteristic which changes based upon the presence of moisture in at least one of the first and second cavities.

This Summary and the Abstract are provided to introduce a selection of concepts in a simplified form that are further described below in the Detailed Description. The Summary and the Abstract are not intended to identify key features or essential features of the claimed subject matter, nor are they intended to be used as an aid in determining the scope of the claimed subject matter.

BRIEF DESCRIPTION OF THE DRAWINGS

FIGS. 5A and 5B are graphically representations of voltage versus time for the output of the moisture sensor circuitry of FIG. 4 when exposed to different amounts of moisture.

DETAILED DESCRIPTION OF ILLUSTRATIVE EMBODIMENTS

A process variable transmitter is provided having a housing with an internal cavity which is divided into first and second cavities. Measurement circuitry located in the first cavity is configured to measure process variable(s) and a terminal block is located in the second cavity. The terminal block is used to couple to external components such as a two-process control loop. A moisture sensor is provided in the second cavity and is configured to sense the presence of moisture in the second cavity. This information can be used to provide a diagnostic output such as a warning to an operator indicating a failure has occurred or that there is an impending failure. The diagnostic output can be sent over a process control loop or can be provided by some other output technique.

Figure 1:
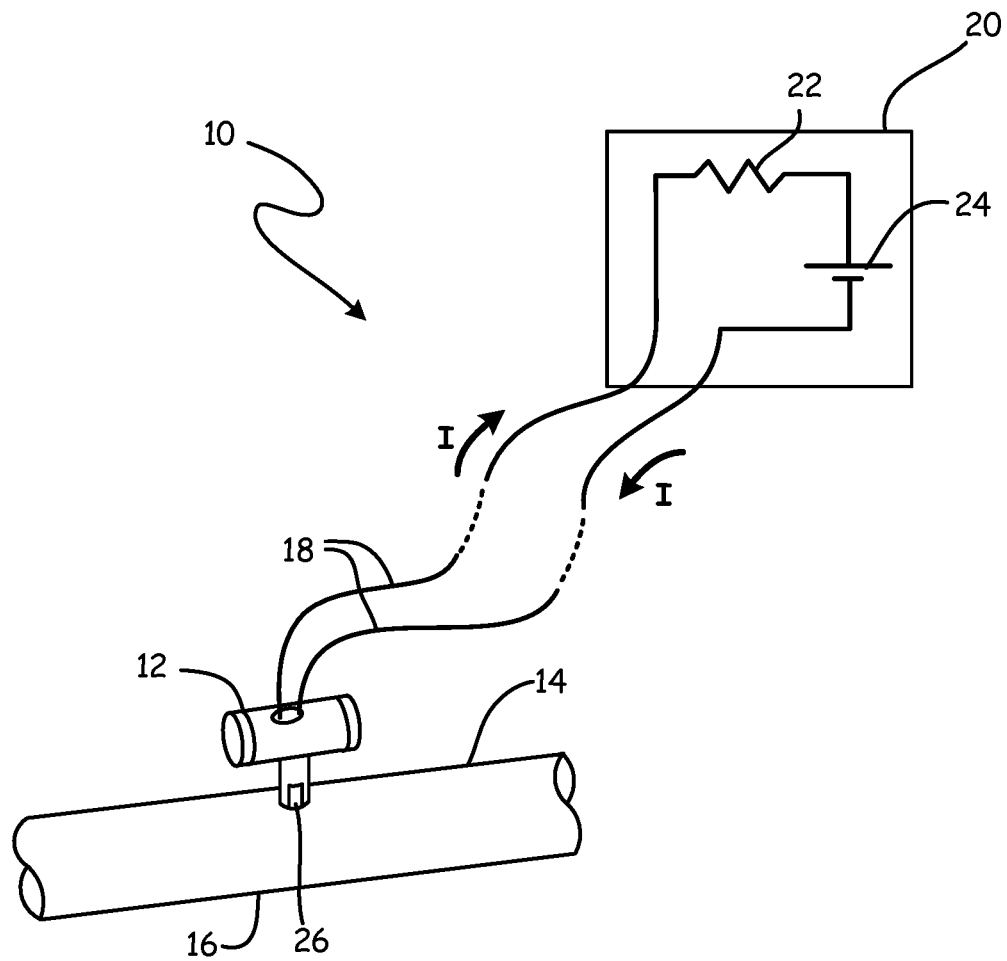
FIG. 1 is a simplified diagram of an industrial process control system including a process variable transmitter configured to sense a process variable of the industrial process.

FIG. 1 is a simplified diagram of an industrial process control or monitoring system 10. System 10 includes a process variable transmitter 12 having a process variable sensor 26 arranged to sense a process variable of a process fluid. In this example, the process fluid is illustrated as contained in process piping 16. The process variable can be any property related to the process fluid such as flow rate, temperature, pressure, pH, etc. The process variable transmitter 12 couples to a two-wire process control loop 18 which carries a loop current I. In the example installation, the process variable transmitter is located at a remote location in the "field" of an industrial process and couples to a control room 20 at, for example, a centralized location through the two-wire process control loop 18. In this example, the control room 20 is illustrated as a sense resistor 22 and a voltage source 24. The transmitter 12 controls the loop current I such that the loop current is representative of the sensed process variable. For example, the loop current may range from 4 mA to 20 mA.

Figure 2:
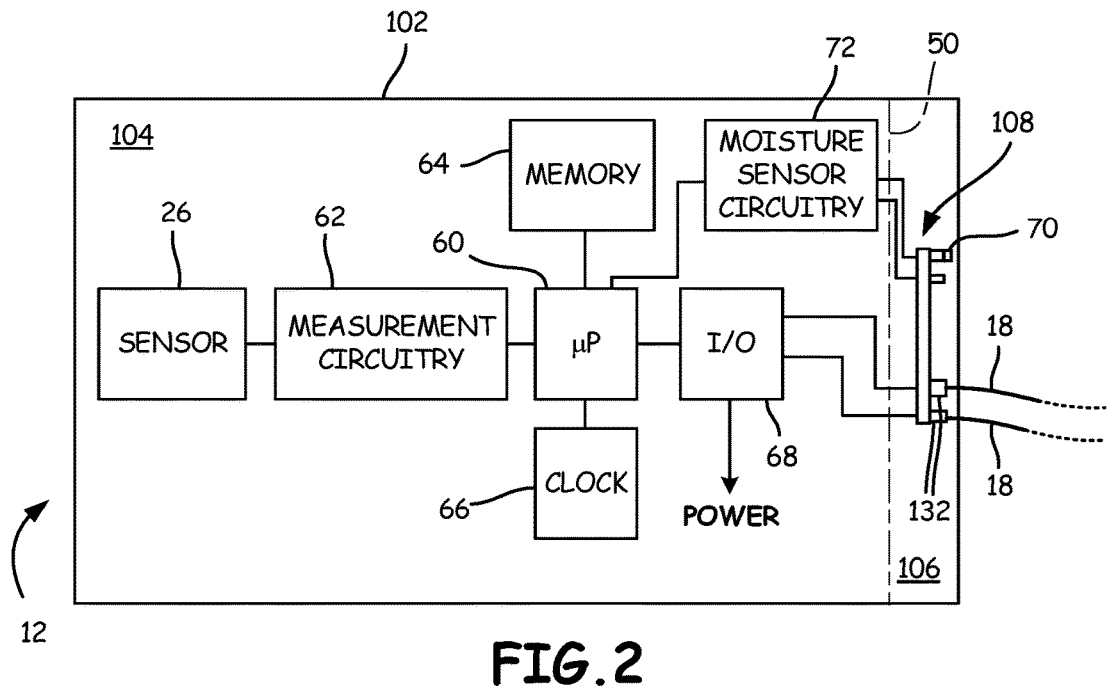
FIG. 2 is a simplified electrical block diagram of the process variable transmitter of FIG. 1.

According to one embodiment, FIG. 2 is a simplified block diagram of process variable transmitter 12 having housing 102 with a cavity formed therein which is divided into a first (electronics) sealed cavity 104 and a second (terminal block) unsealed cavity 106 by barrier 50. A terminal block 108 is located in cavity 106. FIG. 2 illustrates the connection between terminal block 108 and two-wire process control loop 18. The two-wire process control loop 18 may be in accordance with industry standards and is used for transmitting information related to a sensed process variable by the process variable transmitter 12 as well as receiving power to power circuitry of the process variable transmitter 12. One such communication standard is a 4-20 mA communication standard in which an analog current level is used to represent a process variable. A digital signal may also be modulated onto the analog current level to transmit additional information in accordance with the HART® Protocol. The two wire process control loop can also be used for sending information to the process variable transmitter 12. Other types of process control loops may also be used including those in accordance with a Fieldbus standard. Further, the process control loop 18 may be a wireless process control loop in which information is communicated wirelessly. One such wireless communication protocol is the WirelessHART® communication protocol in accordance with IEC 62591. The terminal block 108 is not limited to these types of connections and may include other types of electrical connections or components. Examples include a MODBUS® serial protocol connection or other types of connections for providing power and communications, in both analog and digital formats.

As illustrated in FIG. 2, the first enclosure 104 includes a microprocessor 60 coupled to the process variable sensor 26 through measurement circuitry 62. Microprocessor 60 operates in accordance with instructions stored in memory 64 which may also be used to store other information such as configuration information. Microprocessor 60 operates based upon a clock rate determined by clock 66 and communicates over the process control loop 18 using I/O circuitry 68 through terminal block 108 using connection terminals 132. I/O circuitry 68 may optionally include a power output used to power circuitry of the process variable transmitter 12. In one such configuration, power from the two-wire process control loop 18 is used to wholly power the device.

FIG. 2 also illustrated a moisture sensor 70 carried in the second enclosure 106. In the configuration illustrated in FIG. 2, the moisture sensor is carried on the terminal block 108. However, other configurations may also be employed. Moisture sensor 70 couples to moisture sensor circuitry 72 which is configured to provide an output to microprocessor 60. In operation, the moisture sensor 70 senses moisture and provides an electrical output to the moisture sensor circuitry 72. Moisture sensor circuitry may compare the output to, for example, a threshold level and responsively provide an output to microprocessor 60 providing an indication of the presence of moisture. Similarly, such a determination may also be performed by the microprocessor 60. The moisture sensor 70 may be in accordance with any appropriate technologies and a number of technologies are discussed below.

Typically, moisture accumulates near the terminal block assembly 108 at a relative slow rate such that the level of the moisture rises over time until it eventually contacts the electrical components and terminals of the terminal block 108. This causes a low impedance path (typically less than 10 k ohms) between the terminals 132 and/or the housing 102. On the other hand, a dry terminal block 108 will typically have a leakage resistance of more than 100 M ohms. In one configuration, the moisture sensor 70 is positioned such that any moisture in the second compartment 106 will reach the moisture sensor 70 before it contacts terminals 132 of the terminal block assembly 108. This allows the transmitter 12 to provide a warning output indicating an impending failure. A second moisture sensor can be employed to provide an indication that additional water or other moisture has accumulated. This can be used to provide an output that a failure is imminent. This allows warnings to be sent in the form of an alarm signal before the loop 18 is compromised at which point it may be unable to reliably transmit an alarm signal. The sensor can be automatically checked on a periodic basis, or continually checked for moisture. The moisture sensor 70 can be configured as desired. For example, a single ended configuration may be employed in which a return path of any leakage current through the moisture impedance is provided through the chassis (housing) of the device. A dual ended configuration may also be employed in which two connections are made to the sensor 70 for providing a separate return path.

Figure 3A:
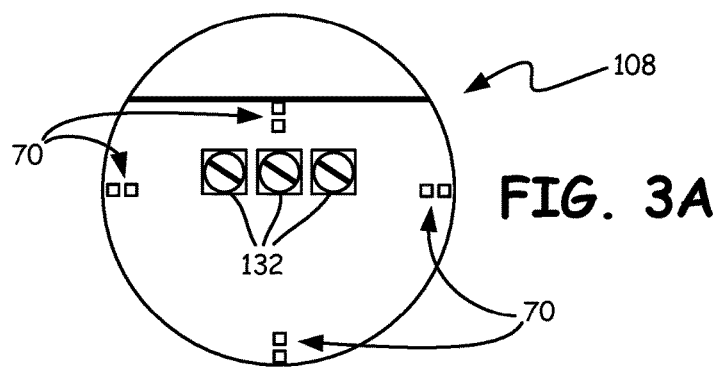
FIG. 3A is a front plan view and FIG. 3B is a side cross-sectional view of one example configuration of a terminal block assembly used in the process variable transmitter of FIG. 1.
Figure 3B:
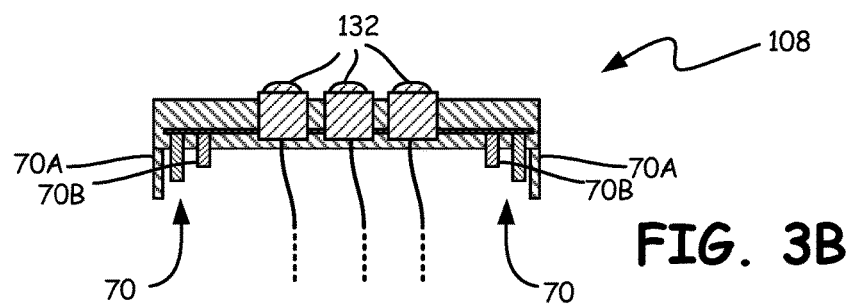

According to one embodiment, FIG. 3A is a front plan view and FIG. 3B is a side cross-sectional view of the terminal block assembly 108. As illustrated in FIG. 3A, the moisture sensor 70 is positioned around an outer edge of the terminal block assembly 108. In the configuration of FIG. 3A, the terminal block assembly is disc shaped and configured to fit within a cylindrical housing 102. The location of the sensors 70 should be chosen as appropriate to obtain warnings based on the presence of moisture at the desired locations to be monitored. In the examples of 3A and 3B, the sensors 70 are positioned around the outer edge of the assembly 108 and configured to surround the terminals 132. Depending on the installation configuration, the transmitter 12 may be rotated 90 degrees. As illustrated in FIG. 3A, four different sensors 70 are positioned at 90 degrees around the outer circumference of the assembly 108. In the example configuration of FIG. 3B, sensor 70 includes a longer warning sensor 70A and a shorter alarm sensor 70B. Sensor 70A is configured to contact a small amount of accumulated moisture and thereby provide an early warning that moisture is building up within the second cavity 106. Sensor 70A is positioned such that it senses moisture just prior to the moisture contacting terminals 132. Sensors 70A and 70B can comprise elongate electrodes or the like. Although the sensors 70A, B are shown as spaced apart individual components, in one configuration the electrodes are configured to span an outer circumference of the terminal block 108. For example, the electrodes may complete a circle around the outer circumference of the terminal block assembly 108.

The moisture sensor electrodes 70A and 70B couple to moisture sensor circuitry 72 shown in FIG. 2. The moisture sensor circuitry may operate in accordance with any appropriate technique to detect impedance changes due to the presence of moisture.

Figure 4:
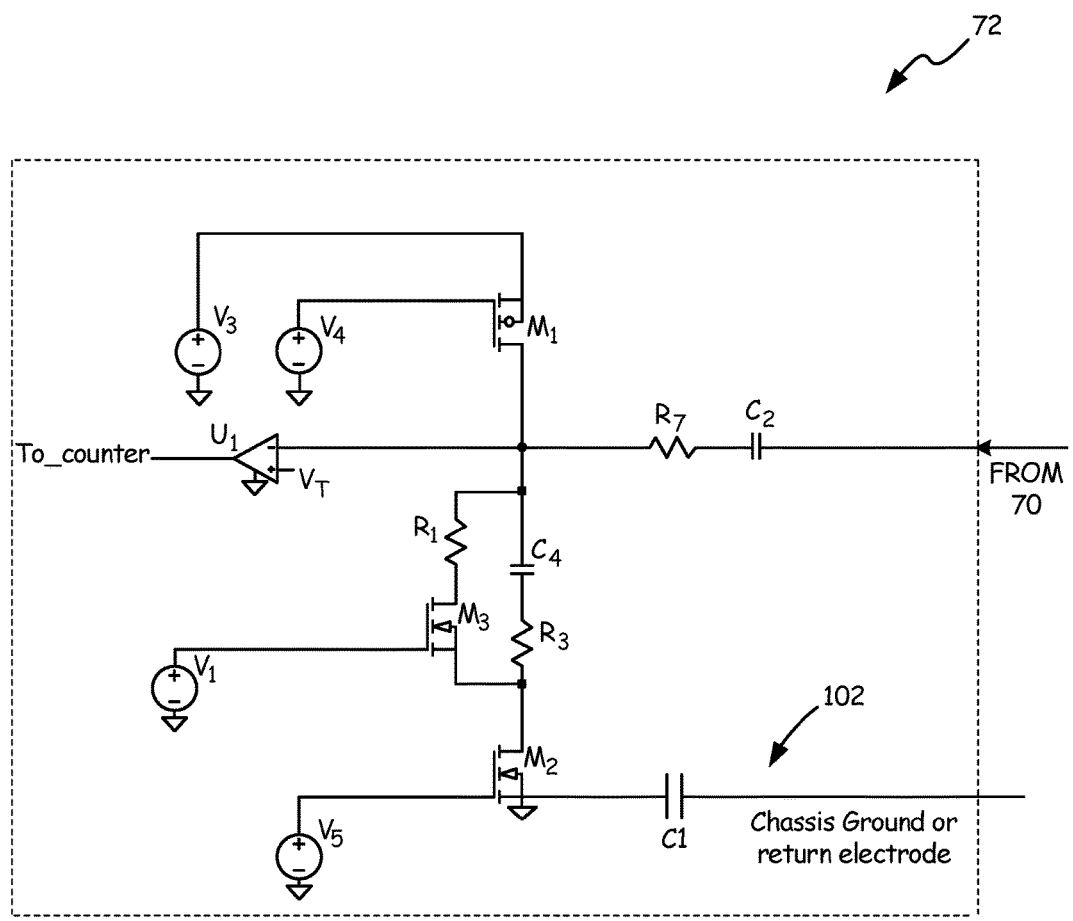
FIG. 4 is a simplified electrical schematic diagram of moisture sensor circuitry for use in sensing moisture proximate the terminal block assembly of FIGS. 3A and 3B.

The impedance measurement can preferably be made with a number of assumptions. It may be assumed that the chassis ground can be at +/−600 VDC or at a +/−600 VDC potential. Further, 50 or 60 Hz noise may be present between the circuitry and the chassis ground. Any appropriate measurement technique may be implemented as desired. FIG. 4 shows one example configuration of moisture sensor circuitry 72. Moisture sensor circuitry 72 operates with a single moisture sensor and a second electrical circuit should be used for two sensors such as 70A, B. In the circuit of FIG. 4, field effect transistors M1, M2 and M3 can be configured to operate under the control of microprocessor 60 shown in FIG. 2. Initially, transistors M1 and M2 are off and transistor M3 is on. This causes an electrical short of the storage capacitors C4 to thereby dissipate any charge. Next, transistors M3 and M2 are turned off and transistor M1 is turned on. This causes transistor C2 to charge through the impedance due to any moisture in contact with the electrodes of the moisture sensor 70 through the return path 102 and capacitor C1. If moisture is present, a larger charge accumulated on C2 whereas a dry system will only accumulate a small charge. Transistors M3 and M1 are then turned off and transistor M2 is turned on. This causes the charge from capacitor C2 to be transferred to C4 through resistance R7. Transistors M3 and M2 are then turned off and transistor M1 is turned back on thereby charging capacitor C2 again. When M1 is on, the comparator input is high and the comparator output drives low. When M2 is on, the comparator input is pulled below the threshold Vt until C4 accumulates enough charge. The comparator output will continue to toggle high and low until the comparator input remains above Vt. Charge is acculated on C4 due to repeating the M1, M2 sequence. This process repeats and the voltage applied to comparator U1 increases with each cycle. When this voltage is greater than a reference voltage $V_T$, the output from comparator U1 remains low. The comparator signal is driven high when M1 turns on. This causes the To_Counter signal to go low. When M1 turns off, and M1 turns on, the comparator signal will initially be driven to a near ground potential. This causes the To_Counter signal to toggle high. As C4 continues to charge (due to repeating the M1, M2 sequence), the voltage on the comparator will transition at the voltage threshold (about 1.25 volts) thereby toggling the To_Counter signal. By counting the toggles of the To_Counter output, the number of charging cycles will indicate the amount of moisture present. A large number of toggles will indicate a low leakage or dry condition and a small number of toggles (cycles) represents a high leakage or wet condition. The threshold count may be adjusted by experimentation to delineate between the selected wet and dry circuit conditions. These steps can be repeated as desired to detect moisture. For example, once per minute, and may be performed along with other background tasks by the microprocessor 60.

FIG. 5A is an example output from comparator U1 when an impedance of 10 M ohms is coupled to circuitry 72. The circuit does not trip until about 125 milliseconds indicating a "dry" condition. In the graph of 5B, the circuit trips at less than 20 milliseconds. This indicates a "wet" condition. The particularly timing threshold can be determined based upon testing or by some other means.

Capacitors C1 and C2 provide a charging path as well as isolate internal measurement circuits from DC voltages that may be present on the chassis of the device. This isolation eliminates potential circuit damage or errors in measurements. Resistor R7 can be used to measure circuit damage due to electrostatic discharge (ESD) or other transient sources. A return path 102 through the chassis ground or other return electronics through capacitor C1 is shown. For metal housings, the moisture will short between the chassis of the device and the sensor and the conduction path will include the device housing. However, for non-conductive configurations, for example with a plastic housing, a second electrode may be included to provide a capacitively coupled path for the charging cycle.

Once a moisture warning or alarm condition is detected, the microprocessor 70 can provide a warning output, for example by setting a warning current level on the process control loop 18 or by providing status information using a digital protocol such as HART Communications.

Figure 6:
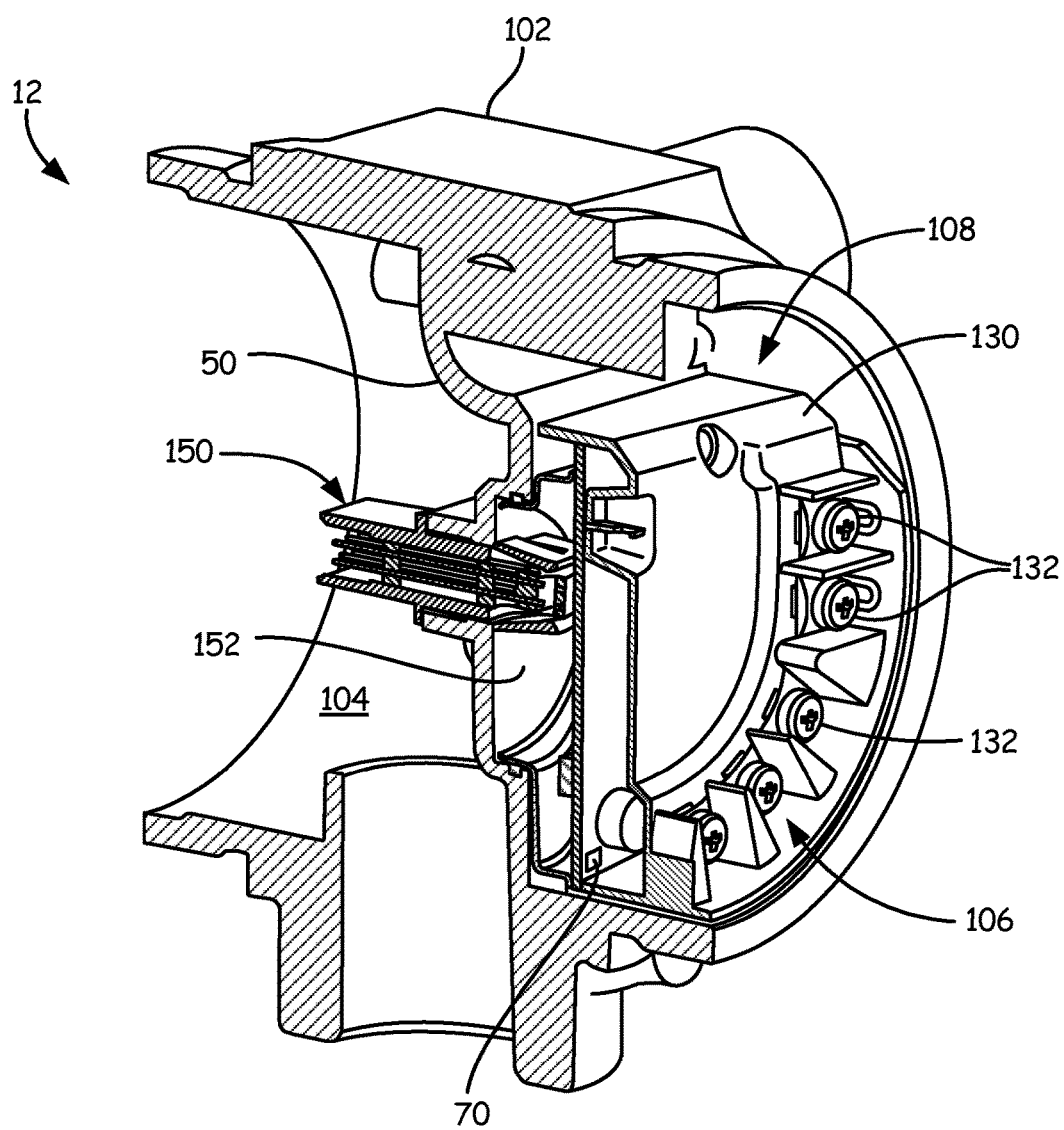
FIG. 6 is a perspective cross-sectional view of another configuration of the process variable transmitter of FIG. 1.
Figure 7:
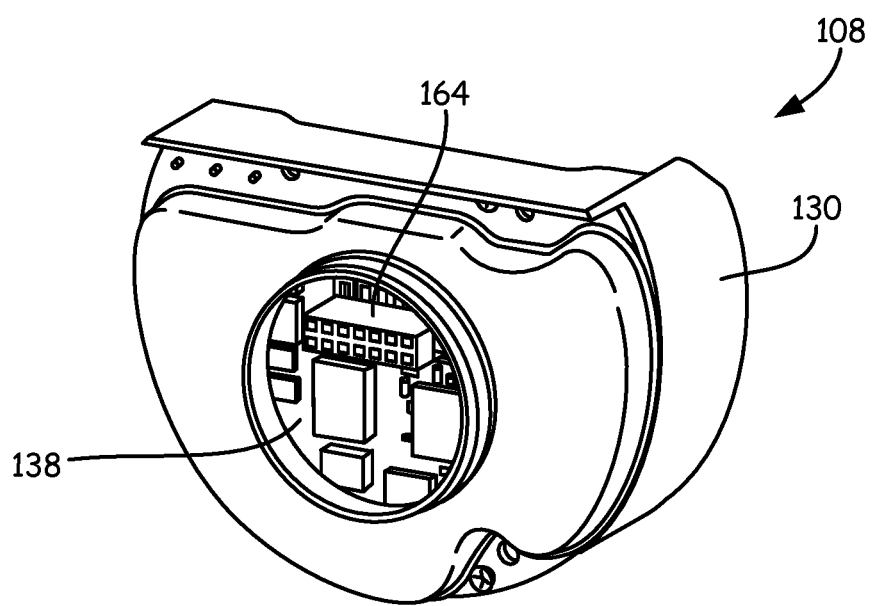
FIG. 7 is a rear perspective view of another example configuration of a terminal block assembly.
Figure 8A:
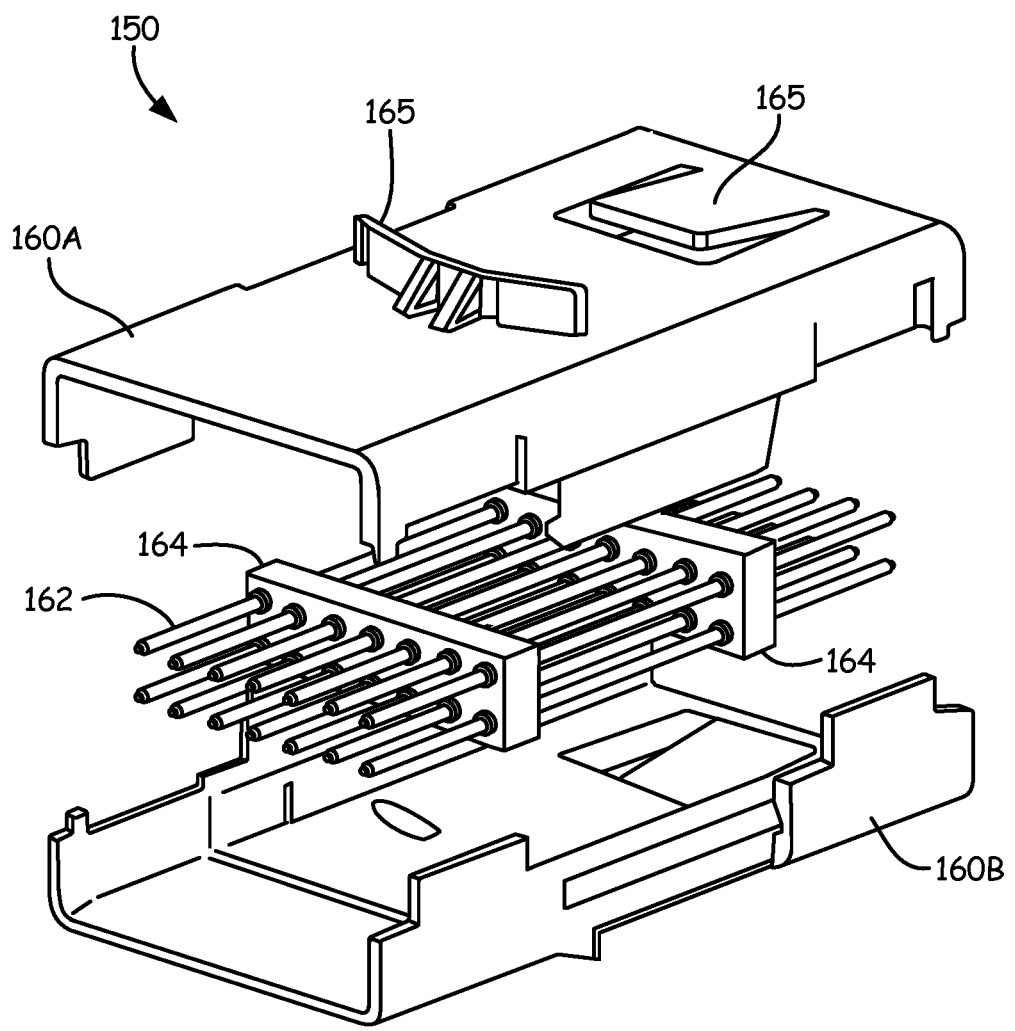
FIG. 8A is an exploded view and 8B is an assembled view of an electrical connector assembly used to electrically connect to the terminal block assembly illustrated in FIG. 7.
Figure 8B:
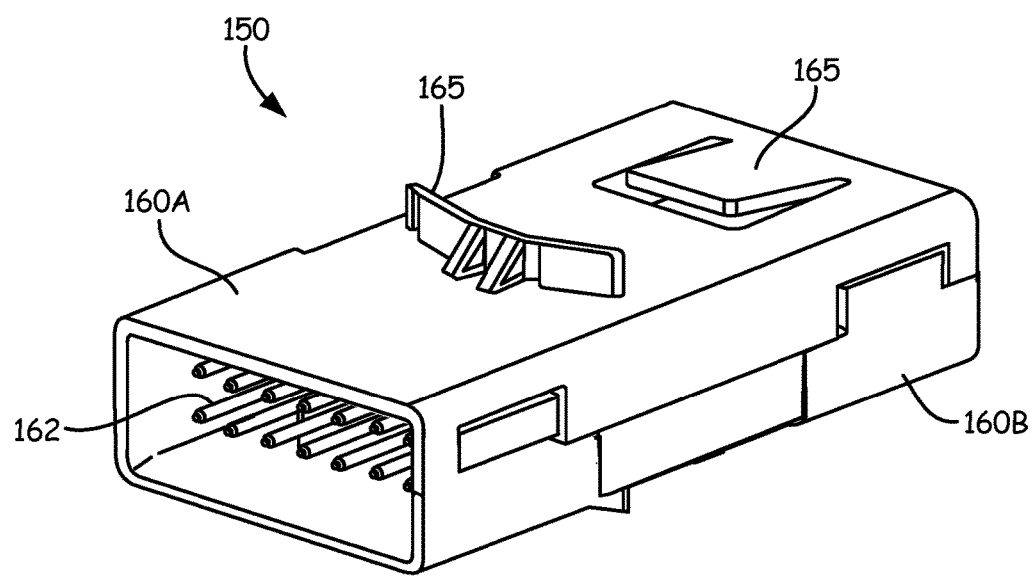

FIG. 6 is a partial cross-sectional view of process variable transmitter 12 including another example configuration of the terminal block assembly 108. Terminal block assembly 108 includes terminal block shroud 130 which carries connectors 132 thereon. Shroud 130 mounts into a recess formed in barrier 50. Barrier 50 also carries an electrical connector assembly 150. Moisture sensors 70 are positioned at desired locations on the housing 130 of the terminal block assembly 108 and are electrically connected to electrical conductors of the electrical connector assembly 150. As illustrated, the electrical connector assembly 150 extends through the barrier 50 and provides electrical connections between the first cavity 104 and the second cavity 106. Further, in this example configuration, the terminal block assembly 108 includes an internal cavity 152 which is arranged to provide a third cavity within the housing 102 of transmitter 12. FIG. 7 is a rear perspective view of the terminal block assembly 108. A circuit board 138 within the shroud 130 carries a female electrical connector 164 for electrically connecting to the electrical connector assembly 150. FIG. 8A is an exploded perspective view and FIG. 8B is a perspective view of the electrical connector assembly 150. Connector assembly 150 is formed in two halves 160A, 160B with electrical conductor pins 162 carried therein. Conductor pins 162 are held in place by supports 164. Tab stops 165 are arranged to secure the electrical connector assembly 150 in position in the barrier 50.

Pursuant to an embodiment, The moisture sensing system for wet terminal block detection discussed herein operates by measuring the impedance between two points. The sensor 70 can be fabricated from two circuit board traces separated by a space. As the humidity level changes, the impedance will change. In a typical application, the warning point should be well defined and set such that water (condensing) across the sensor causes the alert. Normal high humidity should preferably not cause a warning to occur. In one configuration the sensor 70 provides a single connection point which is electrically connected to the moisture sensor circuitry 72 through the barrier 50. A return path for the electrical signal may be provided through the housing 102 in configurations where the transmitter housing 102 is formed of a metal or other conductor. Multiple sensors can be provided using any number of the conductor pins 162 of the electrical connector assembly 150.

Although the present invention has been described with reference to preferred embodiments, workers skilled in the art will recognize that changes may be made in form and detail without departing from the spirit and scope of the invention. The term "moisture" as used herein includes any liquid or gas which is conductive in nature and capable of electrically shorting electrical components. Although a two-wire process control loop 18 is specifically illustrated herein, the configurations are well suited for other communication techniques including a wireless technique. In such a configuration I/O circuitry 68 is configured for wireless communication. The moisture sensors may be carried on the terminal block assembly, mounted on an interior wall of the housing 102, or positioned at some other location within the second cavity 106 as well as positioned in the first cavity 104, or elsewhere within the device. For example, if the cover is not sufficiently tightened on the first cavity 104, moisture may enter the first cavity. The circuitry set forth herein may be used to detect such moisture. Although a passive sensor configuration is illustrated for sensor 70, sensor 70 may also employ active components. Additionally, the moisture sensor circuitry 72 may be carried within the second cavity 106, for example on the terminal block assembly 108. The impedance measurement may be made between a single electrical contact and electrical ground such as that provided by housing 102, or may be made between two individual electrical contacts. The moisture sensor may be positioned or otherwise calibrated to sense different levels of moisture and thereby provide an early warning a final alert. Further, although only two fixed levels of alerts are specifically discussed, a continuous output may also be provided as well as any number of discrete outputs indicating an amount of moisture which is present related to the amount of moisture present in the cavity 106. In one configuration, the moisture sensor is positioned proximate a screw carried on the terminal block which is used for connecting the terminal block to a conductor. In one aspect, a moisture detection circuit is provided which does not disturb other transmitter electronics due to interference from outside sources. Such interference may be due to DC offset voltages or low frequency noise, such as 50 or 60 Hz noise. The isolation is provided to block this interference. In one specific configuration, capacitors are used to provide this isolation.

What is claimed is:

1. A process variable transmitter for use in an industrial process, comprising:
   a sealed housing having a cavity formed therein, the housing including a barrier which divides the cavity into first and second cavities wherein moisture can accumulate in the second cavity with a level that rises as moisture accumulates;
   measurement circuitry in the first cavity configured to measure a process variable of the industrial process;
   a terminal block assembly in the second cavity, the terminal block assembly including electrical terminals and configured to couple to a process control loop; and
   a moisture sensor positioned in the second cavity configured to sense the presence of conductive moisture in the second cavity of the housing when the level of the moisture rises sufficiently to contact the moisture sensor, the moisture sensor having an electrical characteristic which varies when conductive moisture in the second cavities contacts the moisture sensor, the moisture sensor positioned such that moisture in the second cavity contacts the moisture sensor prior to the level of moisture: reaching electrical terminals in the second cavity.

2. The process variable transmitter of claim 1 including a moisture sensor positioned in the first cavity.

3. The process variable transmitter of claim 1 wherein the moisture sensor is mounted on the terminal block in the second cavity.

4. The process variable transmitter of claim 1 wherein the moisture sensor is configured to measure an impedance between a conductor and a return path.

5. The process variable transmitter of claim 4 wherein the return path comprises the housing.

6. The process variable transmitter of claim 1 wherein the moisture sensor comprises first and second electrical conductors having an impedance formed therebetween which changes based upon a presence of conductive moisture.

7. The process variable transmitter of claim 1 including electrical circuitry configured to monitor the electrical characteristic of the moisture sensor.

8. The process variable transmitter of claim 7 wherein the electrical characteristic comprises impedance.

9. The process variable transmitter of claim 7 wherein the electrical circuitry provides a toggled output.

10. The process variable transmitter of claim 9 wherein a number of toggles is related to an amount of conductive moisture present in the at least one of the first and second cavities.

11. The process variable transmitter of claim 9 including a microprocessor configured to detect conductive moisture based upon the toggled output.

12. The process variable transmitter of claim 1 including electrical circuitry configured to compare the electrical characteristic of the conductive moisture sensor with a threshold.

13. The process variable transmitter of claim 1 including a plurality of moisture sensors.

14. The process variable transmitter of claim 13 wherein the plurality of moisture sensors are positioned at an angular offset with respect to one another.

15. The process variable transmitter of claim 14 wherein the angular offset comprises 90 degrees.

16. The process variable transmitter of claim 1 including electrical conductors which extend through the barrier of the housing to the moisture sensor.

17. The process variable transmitter of claim 1 including an output circuitry configured to provide a warning output.

18. The process variable transmitter of claim 17 wherein the warning output is provided on a two wire process control loop.

19. The process variable transmitter of claim 17 wherein the warning output is indicative of an impending failure due to detected conductive moisture.

20. The process variable transmitter of claim 1 wherein the moisture sensor is configured to sense a presence of conductive moisture at a first position and further including a second moisture sensor configured to sense a presence of conductive moisture at a second position.

21. The process variable transmitter of claim 1 wherein the moisture sensor comprises an electrical trace carried on a circuit board.

22. The process variable transmitter of claim 1 wherein the moisture sensor is positioned proximate a screw on the terminal block assembly.

23. The process variable transmitter of claim 1 including isolation circuitry to isolate the measurement circuitry from the interference received through the moisture sensor.

24. The process variable transmitter of claim 23 wherein the isolation circuitry comprises a capacitor.

* * * * *